United States Patent
Picotti et al.

(10) Patent No.: US 10,295,546 B2
(45) Date of Patent: May 21, 2019

(54) METHOD FOR THE DETERMINATION OF CONFORMATION AND CONFORMATIONAL CHANGES OF PROTEINS AND OF DERIVATIVES THEREOF

(71) Applicant: ETH ZURICH, Zurich (CH)

(72) Inventors: Paola Picotti, Zurich (CH); Yuehan Feng, Zurich (CH); Giorgia De Franceschi, Scorze (IT)

(73) Assignee: ETH ZURICH, Zurich (CH)

( * ) Notice: Subject to any disclaimer, the term of this patent is extended or adjusted under 35 U.S.C. 154(b) by 703 days.

(21) Appl. No.: 14/646,823

(22) PCT Filed: Nov. 26, 2013

(86) PCT No.: PCT/EP2013/003564
§ 371 (c)(1),
(2) Date: May 22, 2015

(87) PCT Pub. No.: WO2014/082733
PCT Pub. Date: Jun. 5, 2014

(65) Prior Publication Data
US 2015/0309045 A1   Oct. 29, 2015

(30) Foreign Application Priority Data
Nov. 28, 2012   (EP) .................................... 12008011

(51) Int. Cl.
*G01N 33/68* (2006.01)
*C12Q 1/37* (2006.01)

(52) U.S. Cl.
CPC ............ *G01N 33/6848* (2013.01); *C12Q 1/37* (2013.01); *G01N 2570/00* (2013.01); *G01N 2800/2835* (2013.01)

(58) Field of Classification Search
None
See application file for complete search history.

(56) References Cited

PUBLICATIONS

Zappacosta et al., "Probing the tertiary structure of proteins by limited proteolysis and mass spectrometry: The case of Minibody" Protein Science, 1996, v. 5, pp. 802-813.*

(Continued)

*Primary Examiner* — Lyle Alexander
*Assistant Examiner* — Michelle Adams
(74) *Attorney, Agent, or Firm* — Sughrue Mion, PLLC (57) ABSTRACT

A Method for the detection of the conformational state of a protein contained in a complex mixture of further proteins and/or other biomolecules, is proposed as well as assays for such a method. The method comprises the following steps: (1) Limited proteolysis of the complex mixture under a condition where the protein is in the conformational state to be detected leading to a first fragment sample; (2) Denaturation of the first fragment sample to a denaturated first fragment sample; (3) Complete fragmentation of the denaturated first fragment sample in a digestion step to a completely fragmented sample; and (4) Analytical analysis of the completely fragmented sample for the determination of fragments characteristic of having been the result both the limited proteolysis of step 1 as well as of the complete fragmentation in the digestion step 3. for the determination of the conformational state.

24 Claims, 4 Drawing Sheets
Specification includes a Sequence Listing.

(56) References Cited

PUBLICATIONS

Bantscheff, M. et al. "Probing the tertiary structure of multidomain proteins by limited proteolysis and mass spectrometry," Eur. Mass Spectrom. 4, 279-285 (1998).*

Gudiksen, K. L. et al. "Differentiation of proteins based on characteristic patterns of association and denaturation in solutions of SDS," PNAS May 23, 2006 103 (21) 7968-7972. (Year: 2006).*

Lomenick, B. et al. "Target identification using drug affinity responsive target stability (DARTS)," PNAS Dec. 22, 2009 106 21984-21989 (Year: 2009) (51).*

Doro, F. et al. "Surfonne Analysis as a Fast Track to Vaccine Discovery," Molecular & Cellular Proteomics 2009, 8 (7) 1728-1737 (Year: 2009).*

Ram P. Gupta et al. "Purification and Characterization of Cytochrome P450 Isozymes from , β-Naphthoflavone-Induced Adult Hen Liver", Archives of Biochemistry and Biophysics, Oct. 1990, pp. 170-182, vol. 282, No. 1.

Robin Roychaudhuri et al., "Structural Dynamics of the Amyloid β-Protein Monomer Folding Nucleus", Biochemistry, 2012, pp. 3957-3959, vol. 51.

Alana M. Thackray et al., "Proteinase K-sensitive disease-associated ovine prion protein revealed by conformation-dependent immunoassay", Biochem. J., 2007, pp. 475-483, vol. 401.

Steven L. Cohen et al., "Probing the solution structure of the DNA-binding protein Max by a combination of proteolysis and mass spectrometry", Protein Science, 1995, pp. 1088-1099, vol. 4.

Paola Picotti et al, "Selected reaction monitoring-based proteomics: workflows, potential, pitfalls and future directions", nature methods, Jun. 2012, pp. 555-566, vol. 9, No. 6.

Philip Brownridge et al., "The importance of the digest: Proteolysis and absolute quantification in proteomics", Methods, 2011, pp. 351-360, vol. 54.

Adriano Aguzzi et al., "Protein aggregation diseases: pathogenicity and therapeutic perspectives", Nature Reviews |Drug Discovery, Mar. 2010, pp. 237-248, vol. 9.

Paola Pigotti et al., "Full Dynamic Range Proleome Analysis of S. cerevisiae by Targeted Proteomics", Cell, Aug. 21, 2009, pp. 795-806, vol. 138.

Ludovic C. Gillet et al., "Targeted Data Extraction of the MS/MS Spectra Generated by Data-independent Acquisition: A New Concept for Consistent and Accurate Proteome Analysis", Molecular & Cellular Proteomics 11.6, pp. 10.1074/mcp.0111.016717-1-10.1074/mcp.O111.016717-17 (2012).

Patrizia Polverino De Laureto et al., "Protein Aggregation and Amyloid Fibril Formation by an SH3 Domain Probed by Limited Proteolysis", J. Mol. Biol., 2003, vol. 129-141, vol. 334.

Angelo Fontana et al., "Identifying Disordered Regions in Proteins by Limited Proteolysis", Chapter 20 (2012 ).

Oded Kleifeld et al., "Isotopic labeling of terminal amines in complex samples identifies protein N-termini and protease cleavage products", nature biotechnology, Mar. 2010, vol. 28, No. 3.

Jeffrey R. Whiteaker et al., "An Automated and Multiplexed Method for High Throughput Peptide Immunoaffinity Enrichment and Multiple Reaction Monitoring Mass Spectrometry-based Quantification of Protein Biomarkers", Molecular & Cellular Proteomics 9.1, pp. 184-196.

International Search Report of PCT/EP2013/003564 dated May 16, 2014 [PCT/ISA/210].

Written Opinion of PCT/EP2013/003564 dated May 16, 2014 [PCT/ISA/237].

* cited by examiner

METHOD FOR THE DETERMINATION OF CONFORMATION AND CONFORMATIONAL CHANGES OF PROTEINS AND OF DERIVATIVES THEREOF

CROSS REFERENCE TO RELATED APPLICATIONS

This application is a National Stage of International Application No. PCT/EP2013/003564, filed Nov. 26, 2013, claiming priority based on European Patent Application No. 12 008 011.4, filed Nov. 28, 2012, the contents of all of which are incorporated herein by reference in their entirety.

TECHNICAL FIELD

The present invention relates to methods and tools for the determination of conformation and conformational changes of proteins and of derivatives thereof; optionally in their native biological context, in particular using limited proteolysis combined with selected reaction monitoring.

PRIOR ART

Proteins are crucial effectors and regulators of a wide variety of cellular processes. In response to perturbations (for example, in case of disease), they can change their cellular concentration and their structure. Being able to capture such transitions is an essential task in life sciences, to understand the functioning of basic cellular processes in health and disease and to identify new options for disease diagnosis and treatment. Changes in cellular protein concentration in response to perturbations can be routinely probed by mass spectrometry (MS) based-proteomic techniques. Much less is known about switches in cellular protein conformation, mostly due to the lack of suitable approaches to study protein folds in cells. This is a substantial limitation for biological and clinical applications, since conformational changes can strongly impact protein activity, thus profoundly affecting a cell's physiology.

Proteins can change their conformation upon binding to lipids, ions, small molecules or nucleic acids, interaction with other proteins, chemical modification (e.g. phosphorylation) or environmental changes, such as varying pH or temperature. The extent of a conformational change ranges from small local motions, such as allosteric rearrangements, through larger scale fluctuations, such as domain motions, to the drastic switch between folded and unfolded or monomeric and polymeric states. In particular, the transition of monomeric proteins to higher order aggregated structures has gained increasing attention recently, in both biology and biomedicine. Over the last two decades, a variety of human diseases (more than 20 different pathologies), referred to as protein aggregation diseases were shown to be associated with the intracellular or extracellular accumulation of aggregates of specific misfolded proteins. Many neurodegenerative diseases, such as Parkinson's disease or Alzheimer's disease, of previously unknown aetiology now fall into this category. The different diseases can even be classified according to the major protein components of their aggregates, which also distinguish their clinical manifestations. For example, αSynuclein (αSyn)-containing Lewy bodies are typical for most types of Parkinsonism (PD), while amyloid-$\beta$ peptide inclusions are produced in Alzheimer's disease (see. e.g. A Aguzzi & T O'Connor, *Nat Rev Drug Discov* 9 (3), 237). The possibility of monitoring such protein conformational transitions in biological specimens would open new possibilities for the diagnosis and therapy of these protein-centric conditions and shed light on their pathogenesis.

A number of biophysical techniques have been applied to monitor conformational features of proteins, such as nuclear magnetic resonance (NMR), X-ray crystallography, infrared and Raman spectroscopy, circular dichroism, atomic force microscopy or fluorescence spectroscopy. These techniques are predominantly used to analyze (purified) proteins in vitro, due to their incapability of dealing with complex biological backgrounds. This is a substantial limitation, since the conformation adopted by a protein is regulated in cells by multiple co-occurring events specific to its cellular context, such as environmental cues, binding events or post translational modifications, which cannot be recapitulated by in vitro systems. Techniques based on Förster resonance energy transfer (FRET) offer the advantage of monitoring conformational changes of proteins in their native cellular environment, but require the introduction of fluorescent probes at suitable sites of each target protein and are not applicable on a large scale or on clinical samples.

In light of the above considerations, the availability of methods for tracing protein conformational changes in their biological environment and in a multiplexed manner (multiple proteins at a time) is an urgent requirement. Additional features of an ideal method are: i) suitability for scale-up (fast analysis of multiple samples) and ii) uncomplicated adaptability to different applications (clinical or biotechnological applications or basic research in biology).

SUMMARY OF THE INVENTION

Our invention relates to a new and inventive method that enables identification as well as quantification of protein conformational changes within their native cellular context and proteome-wide, as well as to tools for such a method in particular if applied in the context of the determination of Parkinson's disease as captured by the conformational changes of the system αSynuclein. It is based on the coupling of a biochemical technique called limited proteolysis (LiP) and an advanced targeted mass spectrometry workflow, involving selected reaction monitoring (SRM) or SRM-like approaches (such as SWATH-MS). It is termed Limited-Proteolysis coupled Selected Reaction Monitoring (LiP-SRM) SRM assays are specific, quantitative mass spectrometry-based assays for proteins of interest, akin to antibodies for Western blotting, but with higher multiplexing capabilities and lower development time (assays for 100 peptides can be developed in one hour). We previously demonstrated that SRM allows quantifying proteins in a broad range of cellular abundances, down to <50 copies per cell, in total cell lysates (see P Picotti et al., *Cell* 138 (4), 795 (2009); and Picotti at al. Nature Methods, VOL. 9 NO. 6, June 2012, these references are, as concerns the SRM technique specifically included in the disclosure), resolving proteins with high (>95%) sequence overlap and measuring target peptides across large numbers of samples. Therefore, this technology enables quantitative measurements of specific peptides in very complex samples. Recently, further developments of the SRM approach include SRM-like approaches based on data-independent acquisition of product ion spectra and their targeted analysis (SWATH method, see L C Gillet et al., *Mol Cell Proteomics* 11 (6), O111 016717 (2012), the disclosure of which is included as concerns the SWATH method and the data extraction). The limited proteolysis (LiP) technique on the other hand relies on the application of unspecific proteases for a short time to a protein substrate, so that the initial cleavages are dictated by the conformation of the protein and not by the sequence-specificity of the protease. This translates into reproducible proteolytic patterns that are specific to the conformation of the protein. LiP has been successfully applied to probe domain organization, folding intermediates, ligand-induced conformational changes, protein-protein interactions and protein aggregation (see e.g. P Polverino de Laureto et al., *J Mol Biol* 334 (1), 129 (2003); A. Fontana et al, in Vladimir N. Uversky and A. Keith Dunker (eds.), Intrinsically Disordered Protein Analysis: Volume 2, Methods and Experimental Tools, Methods in Molecular Biology, vol. 896; as concerns the LiP technique these references are specifially included in the specification). However, LiP has so far only been applied to purified proteins (in vitro) due to the challenge of identifying LiP sites in complex backgrounds.

The proposed method couples LiP to an advanced targeted proteomic workflow based on SRM, which enables identification and quantification of LiP products in complex cell extracts. The approach is based on a double protease digestion step, applied to a complete proteome extract (see also FIG. 1).

There are the following steps involved:
1. The first digestion (the LiP step) is conducted in native conditions (in a way that preserves the original protein conformations, i.e. mild treatment, no detergents) with a broad-specificity protease (e.g. proteinase K, PK), at a low enzyme to substrate ratio (E/S) for a short time (e.g. typical setup: PK, E/S=1/100, 5 min). The sites of initial cleavage are dictated by the conformation of the substrate. This typically results in the cleavage of few peptide bonds per protein, thus generating on average large fragments.
2. The proteome is then shifted to denaturing conditions, and complete trypsin digestion is performed, to generate peptides amenable for MS analysis.
3. An aliquot of the same proteome is subjected only to the trypsinization step as a control, to correct for protein abundance changes, trypsin unspecificity and endogenous protease cleavages.

The result is that tryptic peptides embedding the initial LiP cleavage sites are of lower abundance in the doubly digested sample than in the control. Conversely, half tryptic peptides generated by intra-tryptic peptide cleavage appear in the doubly digested sample (see also FIG. 1).

4. Detecting such peptide abundance changes by mass spectrometry (details below) allows to identify the LiP sites and the peptides that are specific to a given protein conformation.

To detect protein conformational differences in different proteome extracts (e.g. healthy and diseased), each proteome is subjected to the double proteolysis step. Each sample is analyzed by targeted liquid-chromatography-coupled mass spectrometry, using either SRM or data-independent acquisition of product ion spectra (SWATH-MS acquisition). In both cases, the targeted peptides are all predicted tryptic peptides for the protein(s) of interest and potential half tryptic peptides, deriving from intra-tryptic peptide cleavage.

The SWATH maps or the SRM peaks from each sample are compared using suitable software tools, thus yielding differently abundant peptides and peptides specific for each conformation (conformotypic peptides). SRM assays for each conformotypic peptide can then be used to quantify the different protein conformations in any biological or clinical sample of interest.

If desired, absolute quantitation can be achieved using heavy-labelled synthetic internal standard peptides. The approach can be directly applied to unfractionated proteome extracts, or it can be coupled to a variety of isotope-labeling and sample fractionation techniques (for example to iTRAQ labeling and the TAILS workflow, O Kleifeld et al., *Nature biotechnology* 28 (3), 281 (2010)), previously used in proteomic experiments. More generally speaking, the present invention relates to a method for the detection of the conformational state of a protein contained in a complex mixture of further proteins and/or other biomolecules, in particular in a complex native biological matrix. The proposed method comprises at least the following steps, carried out, if needed, after an extraction and/or lysis step:

1. Limited proteolysis of the complex mixture under a condition where the protein is in the conformational state to be detected leading to a first fragment sample; in this step there should be no denaturing agents such as detergents present if one wants to capture the conformation in the native state; only those stretches of the amino acid chain will be cleaved which are accessible to the proteolysis, so these will be the regions where there is exposure (location at the periphery) and/or where there is disorder and/or flexibility, which is characteristic for the conformational state of the protein being looked at; the stretches of the amino acid chain which are embedded in rigid tertiary structure and/or buried in the inside will not be affected by this limited proteolysis;
2. Denaturation of the first fragment sample to a denaturated first fragment sample; this step leads to proteins or rather fragments thereof which can subsequently be efficiently and completely be digested to the desired peptides in the subsequent step;
3. Complete digestion (fragmentation) of the denaturated first fragment sample in a digestion step to a completely fragmented/digested sample; this leads to the small and well-defined fragments amenable in particular to selected reaction monitoring techniques;
4. Analytical analysis of the completely fragmented/digested sample for the determination of fragments characteristic of having been the result both the limited proteolysis of step 1. as well as of the complete fragmentation/digestion in the digestion step 3. For the determination of the conformational state; indeed conformationally indicative fragments are those which are affected by both of these steps, since only at sites where cleavage takes place in step 1. there is conformational information available.

It should be noted that when talking about proteins this includes derivatives thereof such as glycoproteins, phosphoproteins or proteins bearing other post-translational modifications.

According to a first preferred embodiment of the proposed method, for the analytical analysis in step 4. mass spectroscopic techniques, in particular specific, quantitative mass spectrometry-based assays, most particularly selected reaction monitoring (SRM) and/or data-independent acquisition of product ion spectra, such as SWATH-MS, are used. Alternatively, the analysis can be performed with shotgun proteomics approaches for the identification and quantitation of the produced fragments.

Preferably, for the detection of the conformational state as such in parallel to steps 1.-3. the original complex mixture is subjected to optionally step 2. and in any case step 3 for the generation of a completely fragmented control sample, wherein this completely fragmented control sample is also subjected to step 4., and wherein the determination of the conformational state of the protein is based on a quantitative comparison of the analytical analysis of the completely fragmented sample with the analytical analysis of the completely fragmented control sample where the LiP step is omitted. So in this case the conformational analysis is carried out based on applying the method to a first sample, and on applying the method without step 1 to generate a control sample. In the control sample there will be no fragments resulting from step 1. So those fragments resulting from step 3. only, will be present in the control sample, while the corresponding stretches in the sample including step 1. will only be part sequences, and the difference between the two is therefore characteristic for the conformational state of the protein.

For the detection of a change of the conformational state depending on different conditions in the complex mixture, on the other hand a first and a second complex mixture is generated by subjecting them to the different conditions, by individually subjecting the two complex mixtures to steps 1.-4., and wherein the determination of the conformational change of the protein is based on a comparison of the analytical analysis of the first completely fragmented sample with the analytical analysis of the second completely fragmented sample. In this case therefore there is no need for a control sample (but it is still recommended as this is required to control for changes in abundance of the protein across different samples), but only the relative proportions are looked at comparing the two complex mixtures. According to yet another preferred embodiment of the proposed method in the step 1. a proteolytic system selected from the group consisting of protease K, Thermolysin, Subtilisin, Pepsin, Papain, α-Chymotrypsin, Elastase, and mixtures thereof is used, preferably at a concentration, with respect to the total biomolecular content in the sample, given as the ratio of enzyme to biomolecular content, in the range of 1/50-1/10000, preferably in the range of 1/100-1/1000 by weight, and wherein further preferably the step is carried out over a time span of 1-60 minutes, preferably in the range of 2-30 minutes, or 2-10 minutes or 2-5 minutes, or in the range of 2-3 minutes.

Preferably the temperature in the limited proteolysis step 1 is in the range of 20-40° C. or 4-90° C. Temperature range is normally at around room temperature (20-25° C.) or at 37° C.; thermolysin on the other hand is active up to 80° C.; 4° C. also applicable to slow down proteolytic reaction.

The properties of the used unspecific proteases are summarized in the table below:

| Protease | Optimal pH | Specificity |
|---|---|---|
| Proteinase K | 7.5-11.0 | Unspecific |
| Thermolysin | 7.0-9.0 | Leu, Phe, Ile, Val, Met, Ala |
| Subtilisin | 7.0-11.0 | Unspecific |
| Pepsin | 1.0-4.0 | Unspecific |
| Papain | 6.0-7.0 | Unspecific |
| α-Chymotrypsin | 7.0-9.0 | Phe, Tyr, Trp, Leu, Ile |
| Elastase | 7.5-8.8 | Ala, Val, Ile, Leu, Gly, Ser, Thr |

Further preferably in step 2. an at least 5 M guanidine hydrochloride concentration is applied for a time span of at least one minute and optionally at a temperature of at least 70° C., preferably of at least 85° C., preferably of around 100° C. These values apply in particular for proteinase K. For other LiP proteases milder denaturants can be sufficient, like urea or guanidinium at a lower concentration and/or temperature.

Preferentially in step 3. A tryptic digestion step is used, preferably at a temperature of 15 to 70° C. over a time span of 2 to 24 hours, at an enzyme to substrate weight ratio in the range of 1/10-1/10000.

For the determination of the conformational state preferably the presence of half tryptic and fully tryptic peptides in the spectra is used.

For quantitative determination heavy labelled fragments characteristic of being the result of both the limited proteolysis of step 1. as well as of the complete fragmentation in the digestion step 3., and/or of the corresponding digestion step only, can be spiked into the original complex mixture or into the completely fragmented sample. Importantly, the presented method can be coupled to an enrichment step based on the application of TAILS workflow to enrich for fragments generated from step 1.

Furthermore the present invention relates to the use of the method as outlined above for the determination of a medically relevant conformation of the protein, for the determination of protein-based drugs, for the influence of drugs or other ligands on proteins, or for quality control of protein-based pharmaceutical preparations.

Last but not least the present invention relates to biomarker assays for use in the above-mentioned method. Specifically the present invention relates to an assay for use in a method as defined above or in use as defined above comprising at least one of the sequences selected from the group SEQ-ID2, SEQ-ID3, SEQ-ID4, SEQ-ID5, or a mixture thereof, preferably as a heavy labelled analogue, in particular in the context of Alzheimer's disease, its determination, the determination of drugs in this context, the determination of the efficiency of drugs in this context.

According to a first preferred embodiment of this biomarker assay this is comprising all four sequences SEQ-ID2, SEQ-ID3, SEQ-ID4, SEQ-ID5 in a mixture, optionally as heavy labelled analogues.

Further embodiments of the invention are laid down in the dependent claims.

The method, combining the LiP method with an advanced SRM-based MS workflow, results in key advantages in comparison to existing techniques. Novelties and advantages of the invention are, inter alia, the following:

1) Applicability to complex biological matrices: This is the first technique that can study protein conformational changes in their native environment and without any perturbation of the system (e.g. FRET requires tagging, hence manipulation of the target protein; NMR, X-ray christallography and also traditional LiP alone are not compatible with complex matrices).

2) High-throughput and multiplexed: By using SRM-MS-based measurements, the proposed method automatically acquires the high throughput and multiplexing capabilities of SRM. This means that analysis of one sample requires about one hour of instrument time and multiple proteins (up to 10016 with SRM, significantly more with SWATH) can be monitored within the same analysis. This is an essential complement to current biophysical and physiochemical methods which probe single proteins.

3) Simplicity: The proposed strategy does not require tedious sample preparation steps such as tagging and purification of the target protein.

4) Transferability: The method can deal with a whole extract background. This can be applied to complex biological backgrounds such as mammalian cell extracts or even body fluids, possibly in combination with enrichment or fractionation steps if necessary.

5) Unbiased or targeted: the method can be used to probe the conformational changes of target proteins of interest. However, it can also be applied in an unbiased manner: i.e. to a whole proteome, to identify which proteins changed conformation in a given condition. These proteome-wide capabilities are not pertaining to any other method. Mapping conformational changes proteome-wide using this technique may become a new level of routine 'omic analysis.

Applications

The proposed method opens numerous possibilities in biomedical, biotechnological and pharmaceutical applications as well as in biological research, only some of them shall be given. It provides a novel platform to measure protein conformational changes, additionally to the conventional protein abundance changes or protein modification changes, currently measured by MS.

- This has particular potential for the detection and treatment (testing new drugs) of diseases caused by protein misfolding and aggregation, such as Alzheimer's or Parkinson's diseases. Conformotypic peptides can be used to probe the structure of disease-related proteins in clinical samples and have potential as disease biomarkers. Furthermore they can be used to test the capability of chemical modulators (drugs) to influence the aggregation process directly in cell extracts, in drug screens.
- This technique can also be applied to monitor stability and proper protein folding of protein-based drugs, an important quality control step for pharmaceutical companies in the production of drugs.
- Since proteins can change conformation upon binding of drugs or other ligands, the method can also be used to identify drug or ligand receptors, based on the detected conformational change.
- Last, it can be used to probe the structure of protein receptors of interest, directly in their cellular matrix, thus aiding the design of molecules to target them.
- The marker assays can be translated into kits for the diagnosis of human diseases (disease biomarkers).
- The method can be used in the drug development pipeline, for quality control of protein-based pharmaceutical preparations.
- It can be used for the development of new drugs for protein conformational diseases.
- It can aid in the identification of receptors of existing drugs, to understand their mechanism of action.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
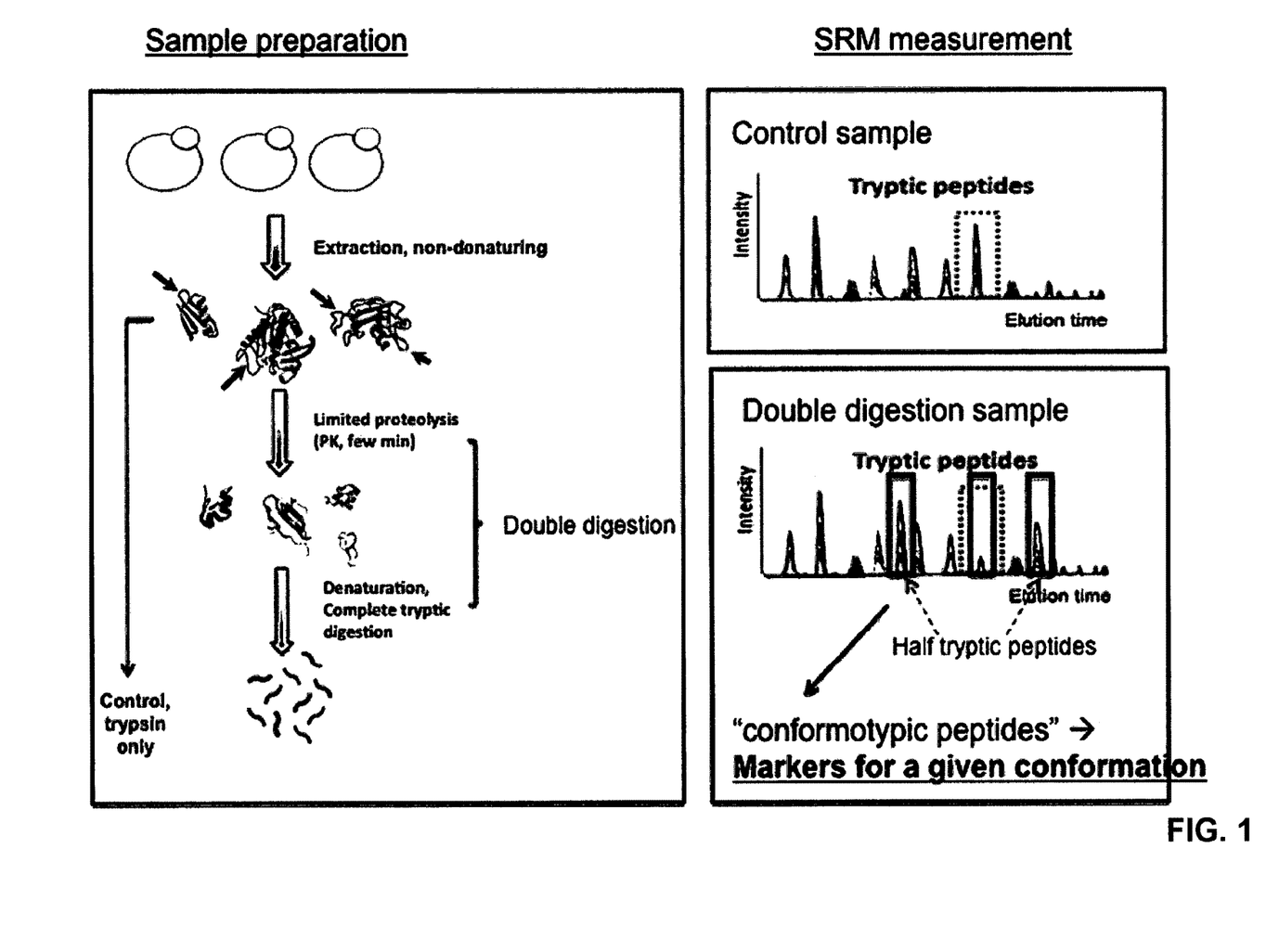
FIG. 1 shows a general overview over the LiP-SRM workflow.

FIG. 1 illustrates in a general overview on the left side of the sample preparation step, and on the right side the analytical part. In the sample preparation step, which is typically preceded by the known processes of lysis of the actual sample system which can be a e.g. cell extract (in case of body fluid, the lysis step is not necessary) in a first step applied to the original sample, under non-denaturing conditions so as to keep the conformation, the limited proteolysis step is carried out, typically under low enzyme concentration, free from detergents and over a short time span at mild temperatures. Subsequently the fragments generated thereby are completely denatured, e.g. by exposure to guanidinine hydrochloride, urea or other denaturants in high concentrations of several M, optionally at high temperatures of typically almost boiling temperature, and over time span of several minutes, to make sure that the proteolytic systems of the first step are inactivated. Subsequently there is a complete tryptic digestion step.

In parallel, a second fraction of the original sample is directly subjected to the same denaturation and complete tryptic digestion for the control.

An example of a typical readout is given on the right side, on the upper part the measurement for the control is shown, in the lower part of the measurement of the double digestion sample:

The fully tryptic peptide detected in the control sample appears cleaved by the unspecific protease in the double-digested sample. Hence, the signal of the tryptic peptide significantly decreases and simultaneously, two half-tryptic peptides become detectable in the double-digested sample. In such manner, a unique proteolytic pattern is generated, including specific conformotypic peptides for each protein in a given conformation.

As Concerns the Lysis Step which can Precede the Method, this can be Carried Out as Follows (as an Example):

Yeast Cell Lysis:

Buffer H: 20 mM HEPES, 150 mM KCl, 15 mM MgCl2

Yeast cells are harvested from liquid culture by centrifugation at 3000 rcf for 5 minutes at 4° C. The pellet is then washed 3 times with buffer H and shock-frozen using liquid nitrogen. To break the cells, a freezer mill system is applied. Protein concentration after the lysis is determined by bicinchoninic acid assay (BCA Protein Assay Kit, Thermo Scientific).

Mammalian Cell Lysis

Extraction buffer (5 ml aliquots): 20 mM Tris pH 7.5; 100 mM NaCl; 20 mM β-glycerolphosphate; 5 mM MgCl2; 0.2% NP-40; 10% glycerol; 1 mM NaF Add immediately before use: 0.5 mM DTT; Protease inhibitor mix; 100× Complete (tablets)

1. Scrape off cells from dish and centrifuge for 5 minutes at 1500 rpm in a Heraeus Biofuge at 4° C.

2. Wash cell-pellet once with 10 ml ice-cold PBS and then dry pellet as good as possible. At this stage one can freeze the pellet either short-term (maximally over the weekend) in −20° C. or long term after shock-freezing (liquid nitrogen) at −80° C. (more stable than in extraction buffer)

3. Resuspend cell pellet corresponding to 1 10 cm dish in 100-200 ul ice-cold extraction buffer and transfer to 1.5 ml Eppendorf tube 4. Either incubate for ½ on ice or perform pottering. Pottering procedure: Move the pistil (syringe: 1 ml, 26 G×1/2, 0.45×12 mm) 3×3-5' slowly up and down during ~15 minutes on ice.

5. Centrifuge for 10 min at 13000 rpm at 4° C. in order to pellet the bulk DNA and RNA for immunoprecipitation. Put supernatant into new Ependorf tube. Measure concentration of extracts with BCA assay.

The Protocol for the Step of Limited Proteolysis (LiP) and Subsequent Sample Preparation for Mass Spectrometry can be as Follows (as an Example):

To prepare before one starts:
Buffer H: 20 mM HEPES, 150 mM KCl, 15 mM MgCl2
Protease of choice diluted to appropriate concentration
Whole cell extract (WCE) with known protein concentration (please refer to lysis protocols)
71 mg guanidine hydrochloride (GdnHCl) in 1.5 ml Eppendorf tubes resuspended in 30 µl 1× Buffer H 1) Adjust carefully the pH of all protein extracts to 7-7.5

2) Dilute WCE such that the total protein concentrations of all samples reach 2 µg/µl and for each sample, aliquots of 30 µl (60 µg) is taken to Eppendorf tubes.

3) For control sample (trypsin only), one aliquot of 30 µl is added directly to the readily prepared GdnHCl tube described above and vortexed thouroughly.

4) For LiP sample, the protease of choice is added to one aliquot of 30 µl sample at optimal enzyme to substrate ratio and incubated for a defined time.

5) The LiP process is stopped by transferring the reaction mixture to the prepared tubes containing presolved GdnHCl so that the final GdnHCl concentration reaches 7.5M. The tube is then vortexed thoroughly and boiled for few minutes.

6) Alternatively, the LiP process can be stopped by adjusting the pH value such that the protease is deactivated.

MS Sample Preparation:

7) Dithiothreitol is added to all samples at a final concentration of 12.5 mM and incubated for 30 minutes at 37 degrees.

8) Iodoacetamide is added to all samples at a final concentration of 40 mM and incubated for 30 minutes at 25 degrees.

9) Dilute all samples with buffer H so that the GdnHCl concentration is below 0.5M.

10) Add trypsin at a w/w ratio of 1:100 and incubate at 32 degrees overnight. MS sample cleanup:

11) Stop the trypsin digestion reaction by decreasing the pH of the mixture to at least 3.

12) Use commercial C18 columns to cleanup the peptides. (e.g. http://www.waters.com/waters/partDetail.htm?partNumber=WAT054955)

Application to a Disease-Related Protein: Alpha-Synuclein

The proposed method was applied to the protein alpha-Synuclein (αSyn, human, with SEQ-ID1 as illustrated in FIG. 1), with the double purpose of
i) testing whether the method can detect different conformations of the same protein in a complex background and
ii) extracting conformotypic peptides for different conformations adopted by this medically-relevant protein, as potential disease biomarkers.

Conformation-specific proteolytic patterns of four conformational states of αSyn (see FIG. 2) were explored. This protein plays a central role in the pathogenesis of Parkinson's disease (PD) and has been found as a major constituent of cytoplasmic protein aggregates in the neurons of PD patients. αSyn has been shown in previous in vitro studies to be predominantly unfolded in its monomeric state. However, when it forms amyloid fibrils (the pathological conformation), it adapts to a rigid β-sheet fold and aggregates with molecules of the same species.

Figure 2:
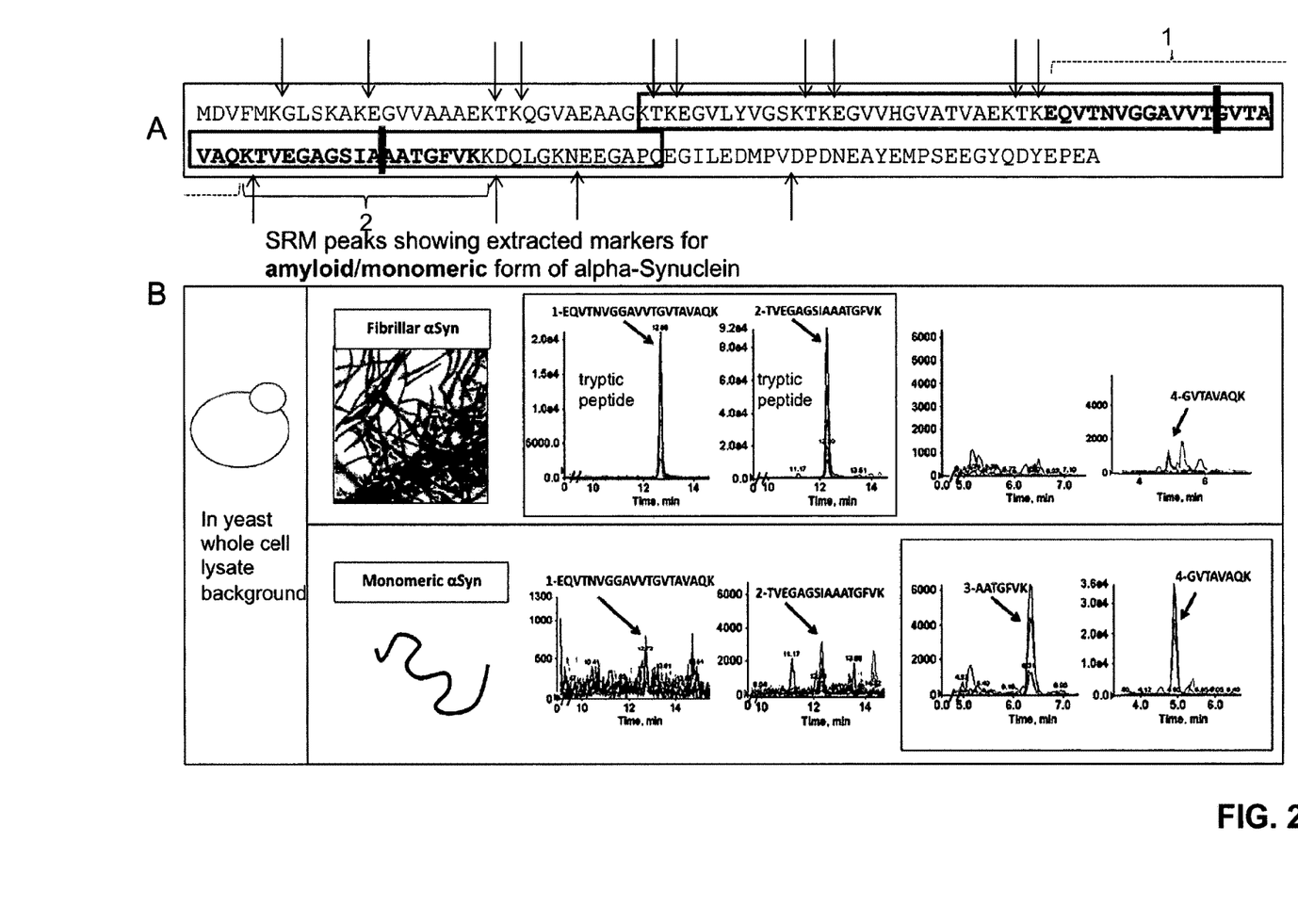
FIG. 2 shows in (A) the amino acid sequence of αSyn and conformotypic peptides for different αSyn conformations; the amyloid core is indicated by the box; the two signature peptides used as conformational markers are indicated by the brackets 1 and 2; cleavage sites of proteinase K on those peptides are shown by the vertical lines, and the tryptic cleavage sites are indicated by arrows; in (B) SRM peaks showing "conformotypic" peptides for αSyn in its fibrillar and monomeric state; both measurements were done in a yeast whole cell lysate background, the double-digested samples are shown here.

To extract the aforementioned proteolytic patterns as markers for the pathological and functional conformations of αSyn, we first prepared in vitro αSyn, in different conformational states. To mimic a complex cellular background, we spiked each αSyn conformation into a yeast whole cell lysate respectively and applied to each lysate the LiP-SRM method. The MS analysis yielded conformotypic peptides for the monomeric and fibrillar conformations of αSyn, respectively. SRM assays for these peptides demonstrated the abundance (and thus conformational) differences in the two samples.

Peptides EQVTNVGGAVVTGVTAVAQK (SEQ-ID2) and TVEGAGSIAAATGFVK (SEQ-ID3), mapping to the core amyloid region of αSyn (ref 30) are protected and thus abundant for the fibrillar conformation of αSyn. These peptides are therefore conformotypic peptides for the fibrillar state of the protein. Their fragments, GVTAVAQK (SEQ-ID5) and AATGFVK (SEQ-ID4) are produced upon PK cleavage only in the sample containing the monomeric conformation, where this region is disordered. These peptides are therefore conformotypic peptides for the monomeric state.

Therefore our method identified peptides specific for different conformations of αSyn, in whole cell extracts and provided specific (SRM) assays to quantify the protein conformers in different samples. Furthermore, these data show that LiP-SRM can overcome the previous limitations and enable the quantitation of different conformational states of proteins in complex matrices.

Figure 3:
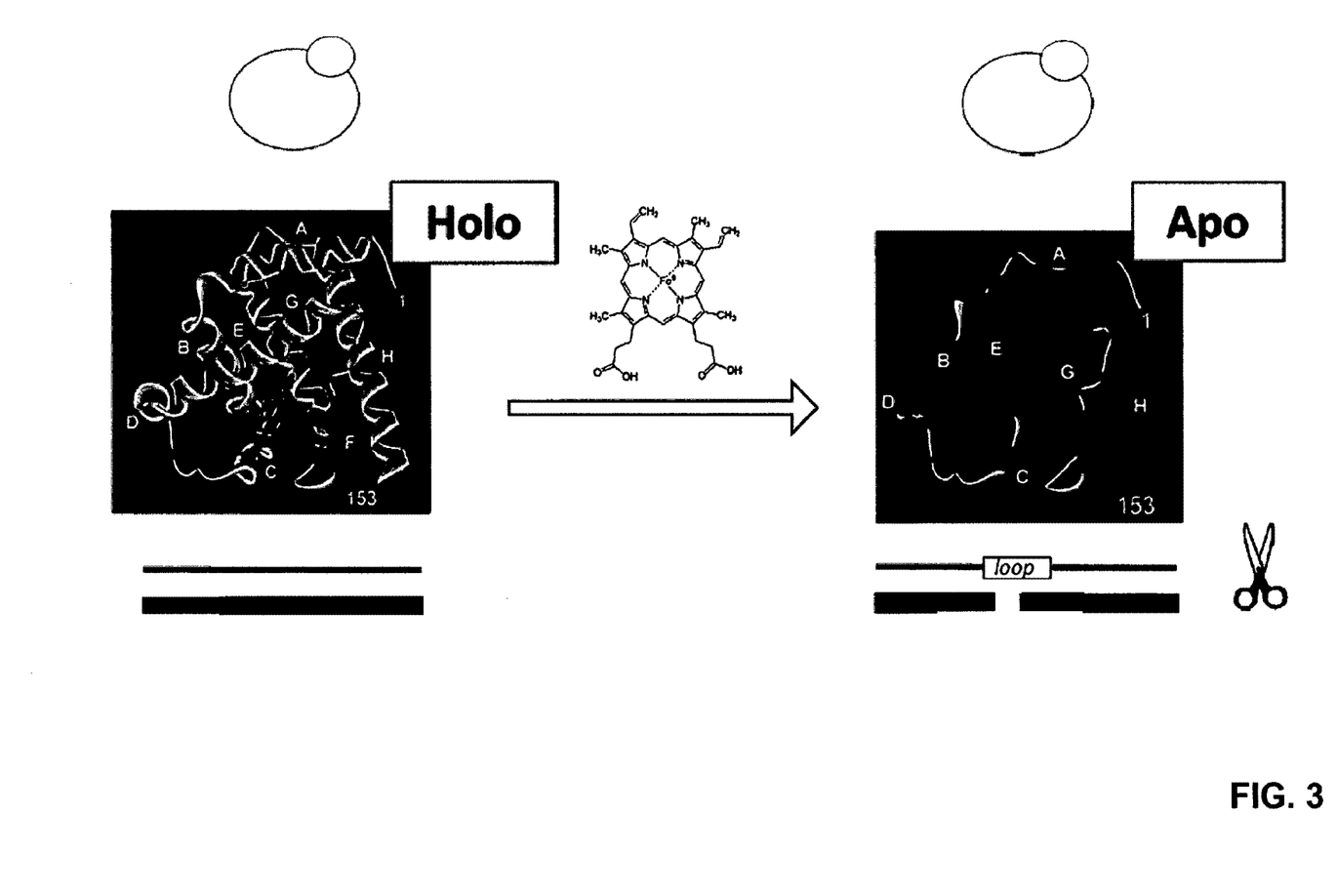
FIG. 3 shows a schematic view of the conformational change of the myoglobin system.

Application to Myoglobin:

The experiments conducted on alpha-synuclein captured a substantial conformational change of a protein, from predominantly disordered, to a β-sheet-rich amyloid state. To assess whether the method is also capable of capturing more subtle conformational changes, affecting only small portions of a protein structure, it is also applied to a second model system, comprising different conformations of the protein myoglobin (horse), spiked into a cell proteome background. (Holo)Myoglobin (H-Mb) is a small globular protein (SEQ-ID6), whose structure comprises 8 α-helices. When its prosthetic group heme is removed from H-Mb, the apo conformational form of myoglobin (A-Mb) is generated (see FIG. 3, removal of heme from left to right). The structure of A-Mb was shown by different techniques to resemble that of H-Mb with the only difference being the local unfolding of helix F in A-Mb. Disruption of a single helix to generate an intramolecular loop is hypothesized to result from the loss of a helix-stabilizing interactions between the heme group and the polypeptide region encompassing helix F.

Figure 4:
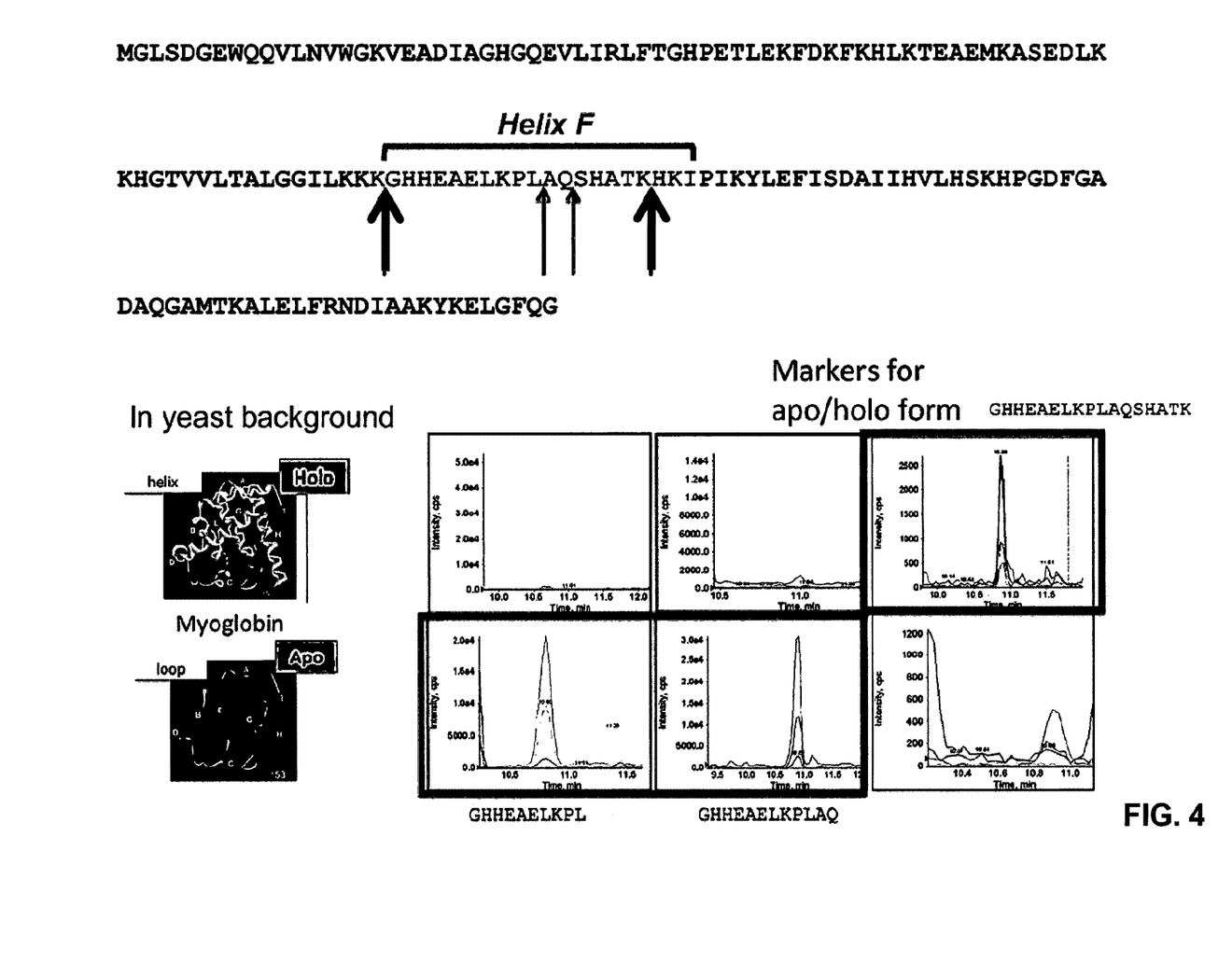
FIG. 4 shows in the upper part the amino acid sequence of myoglobin; the helix F region is shaded, tryptic cleavage sites are indicated by thick arrows whereas LiP sites (with proteinase K) are indicated with thin arrows; in the lower part SRM peaks showing "conformotypic" peptides for myoglobin in its Holo (with helix F) and Apo (without helix F) state are given; both measurements were done in a yeast whole cell lysate background, the double-digested samples are shown.

The myoglobin model is therefore an optimal test-case to assess the capability of the proposed method to detect subtle conformational changes (local unfolding of a single α-helix). We prepared samples containing the two different myoglobin conformations as previously described, spiked them separately into whole yeast proteome extracts and analyzed the resulting samples with the LiP-SRM workflow. The LiP step resulted in the selective cleavage of the region encompassing helix F in the crystal structure of H-Mb (proteinase K cleaves the PL-AQ and/or the AQ-SH peptide bond). We could detect peptide GHHEAELKPLAQSHATK (SEQ-ID7) predominantly in the H-Mb/yeast mixture. Half trpytic peptides GHHEAELKPL (SEQ-ID8) and GHHE-AELKPLAQ (SEQ-ID9) deriving from internal cleavage of the same peptide were detected preferentially in the A-Mb/yeast sample (the KP bond is generally not cleaved by trypsin). Therefore, the LiP-SRM approach could successfully probe the two conformational states of myoglobin, even if they involved less than 15% of the myoglobin sequence. It allows allowed to identify suitable conformotypic markers for the two conformations, which can be used to probe the structural transitions of the protein in a quantitative manner and in a complex cellular background.

Sequences:
SEQ-ID1:
MDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQL

GKNEEGAPQEGILEDMPVDPDNEAYEMPSEEGYQDYEPEA

SEQ-ID2:
TVEGAGSIAAATGFVK

SEQ-ID3:
EQVTNVGGAVVTGVTAVAQK

SEQ-ID4:
AATGFVK

SEQ-ID5:
GVTAVAQK

SEQ-ID6:
MGLSDGEWQQVLNVWGKVEADIAGHGQEVLIRLFTGHPETLEKFDKFKHL

KTEAEMKASEDLKICHGTVVLTALGGILKICKGHHEAELKPLAQSHATIC

HKIPIKYLEFISDAIIHVLHSKHPGDFGADAQGAMTKALELFRNDIAAKY

KELGFQG

SEQ-ID7:
GHHEAELKPLAQSHATK

SEQ-ID8:
GHHEAELKPL

SEQ-ID9:
GHHEAELKPLAQ

The invention claimed is:

1. A method for the detection of a conformational state of a protein, said protein contained in a complex cell extract mixture of further proteins, other biomolecules, or both, comprising the following steps:
   limited proteolysis of a first sample of the complex cell extract mixture under a native condition, in which native condition the protein is in an original conformational state to be detected, leading to a first fragment sample;
   denaturation of the first fragment sample to a denaturated first fragment sample;
   enzymatic digestion of the denaturated first fragment sample to a first digested sample;
   analytical analysis of the first digested sample using at least one of selected reaction monitoring (SRM) and data-independent acquisition of product ion spectra;
   denaturation of a second sample of the complex cell extract mixture to a denaturated second fragment sample;
   enzymatic digestion of the denaturated second fragment sample to a second digested sample;
   analytical analysis of the second digested sample using at least one of selected reaction monitoring (SRM) and data-independent acquisition of product ion spectra; and
   determining the conformational state of the protein using a quantitative comparison of the analytical analysis of the first digested sample with the analytical analysis of the second digested sample.

2. The method according to claim 1, wherein in the limited proteolysis step, a proteolytic system selected from the group consisting of protease K, thermolysin, subtilisin, pepsin, papain, α-chymotrypsin, elastase, and mixtures thereof, is used.

3. The method according to claim 1, wherein in the limited proteolysis step, a proteolytic system is used at a concentration, with respect to the total biomolecular content in the complex cell extract mixture, given as a ratio of enzyme to biomolecular content, in a range of 1/50-1/10000 by weight.

4. The method according to claim 1, wherein in the limited proteolysis step, a proteolytic system is used at a concentration, with respect to the total biomolecular content in the complex cell extract sample, given as the ratio of enzyme to biomolecular content, in the range of 1/100-1/1000 by weight.

5. The method according to claim 1, wherein the limited proteolysis step is carried out over a time span of 1-60 minutes.

6. The method according to claim 1, wherein the limited proteolysis step is carried out over a time span of 2-30 minutes.

7. The method according to claim 1, wherein limited proteolysis step is carried out over a time span of 2-10 minutes, at a temperature range of 20-40° C.

8. The method according to claim 1, wherein in the denaturation of the first fragment sample, an at least 5 M guanidine hydrochloride concentration is applied to the first fragment sample for a time span for at least one minute.

9. The method according to claim 1, wherein at least 5 M guanidine hydrochloride concentration is used in at least one of the enzymatic digestion steps for a time span of at least one minute and at a temperature of at least 70° C.

10. The method according to claim 1, wherein at least 5 M guanidine hydrochloride concentration is used in at least one of the enzymatic digestion steps for a time span of at least one minute and at a temperature of at least 85° C.

11. The method according to claim 1, wherein trypsin is used in at least one of the enzymatic digestion steps.

12. The method according to claim 1, wherein in determining the conformational state, presence of half tryptic fragments in a spectrum is used.

13. The method according to claim 1, wherein for quantitative determination, heavy labelled fragments characteristic of being the result of both the limited proteolysis step and of at least one of the enzymatic digestion steps, and/or of a digestion step only, are spiked into the complex cell extract mixture or into the first digestion sample and/or the second digestion sample.

14. The method according to claim 1, wherein a biomarker assay is spiked in the complex cell extract mixture or in the first digestion sample and/or the second digestion sample, comprising at least one of the sequences selected from the group consisting of SEQ ID NO: 2, SEQ ID NO: 3, SEQ ID NO: 4, SEQ ID NO: 5, and a mixture thereof.

15. The method according to claim 14, wherein the biomarker assay comprises all four sequences SEQ ID NO: 2, SEQ ID NO: 3, SEQ ID NO: 4, and SEQ ID NO: 5, in a mixture as heavy labelled analogues.

16. The method according to claim 1, wherein a biomarker assay is spiked into the complex cell extract mixture or into the first digested sample and/or the second digested sample, comprising at least one sequence selected from the group consisting of SEQ ID NO: 2, SEQ ID NO: 3, SEQ ID NO: 4, and SEQ ID NO: 5, and a mixture thereof, as a heavy labelled analogue(s).

17. The method according to claim 16, wherein the biomarker assay is for Parkinson's disease determination, determination of drugs in the context of Parkinson's disease, and/or determination of the efficiency of drugs in the context of Parkinson's disease.

18. The method according to claim 1, for the determination of a medically relevant conformation of the protein, for the determination of protein-based drugs, for the influence of drugs or other ligands on proteins, or for quality control of protein-based pharmaceutical preparations.

19. The method according to claim 1, wherein peptide fragment enrichment techniques are used for peptides generated by the limited proteolysis (LiP) step.

20. The method according to claim 1, wherein peptide fragment enrichment techniques in the form of terminal amine isotope labelling of samples (TAILS) are used for peptides generated by the limited proteolysis (LiP) step.

21. The method according to claim 1, wherein the complex cell extract mixture is a complex native biological matrix.

22. The method according to claim 1, wherein the steps of limited proteolysis, denaturation of the first fragment sample, enzymatic digestion of the denatured first fragment sample, and analytical analysis of the first digested sample, are carried out after at least one of an extraction or lysis step.

23. The method according to claim 1, wherein specific, quantitative mass spectrometry-based assays are used for at least one of the analytical analysis steps.

24. The method according to claim 1, wherein at least one of SWATH-MS (sequential window acquisition of all theoretical mass spectra) and data-dependent acquisition is used for at least one of the analytical analysis steps.

* * * * *

SEQUENCE LISTING

<160> NUMBER OF SEQ ID NOS: 9

<210> SEQ ID NO 1
<211> LENGTH: 140
<212> TYPE: PRT
<213> ORGANISM: Homo sapiens
<220> FEATURE:
<223> OTHER INFORMATION: alpha-Synuclein

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 16
<212> TYPE: PRT
<213> ORGANISM: Homo sapiens
<220> FEATURE:
<223> OTHER INFORMATION: peptide

```
<400> SEQUENCE: 2

Thr Val Glu Gly Ala Gly Ser Ile Ala Ala Ala Thr Gly Phe Val Lys
1               5                   10                  15

<210> SEQ ID NO 3
<211> LENGTH: 20
<212> TYPE: PRT
<213> ORGANISM: Homo sapiens
<220> FEATURE:
<223> OTHER INFORMATION: peptide

<400> SEQUENCE: 3

Glu Gln Val Thr Asn Val Gly Gly Ala Val Val Thr Gly Val Thr Ala
1               5                   10                  15

Val Ala Gln Lys
            20

<210> SEQ ID NO 4
<211> LENGTH: 7
<212> TYPE: PRT
<213> ORGANISM: Homo sapiens
<220> FEATURE:
<223> OTHER INFORMATION: fragment of peptide SEQ ID 2

<400> SEQUENCE: 4

Ala Ala Thr Gly Phe Val Lys
1               5

<210> SEQ ID NO 5
<211> LENGTH: 8
<212> TYPE: PRT
<213> ORGANISM: Homo sapiens
<220> FEATURE:
<223> OTHER INFORMATION: fragment of peptide SEQ ID 3

<400> SEQUENCE: 5

Gly Val Thr Ala Val Ala Gln Lys
1               5

<210> SEQ ID NO 6
<211> LENGTH: 154
<212> TYPE: PRT
<213> ORGANISM: Equus caballus
<220> FEATURE:
<223> OTHER INFORMATION: Holo-Myoglobin

<400> SEQUENCE: 6

Met Gly Leu Ser Asp Gly Glu Trp Gln Gln Val Leu Asn Val Trp Gly
1               5                   10                  15

Lys Val Glu Ala Asp Ile Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Thr Val Val Leu Thr Ala Leu Gly Gly Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Asp Ala Ile
            100                 105                 110
```

```
Ile His Val Leu His Ser Lys His Pro Gly Asp Phe Gly Ala Asp Ala
        115                 120                 125

Gln Gly Ala Met Thr Lys Ala Leu Glu Leu Phe Arg Asn Asp Ile Ala
        130                 135                 140

Ala Lys Tyr Lys Glu Leu Gly Phe Gln Gly
145                 150

<210> SEQ ID NO 7
<211> LENGTH: 17
<212> TYPE: PRT
<213> ORGANISM: Equus caballus
<220> FEATURE:
<223> OTHER INFORMATION: peptide of SEQ ID 6

<400> SEQUENCE: 7

Gly His His Glu Ala Glu Leu Lys Pro Leu Ala Gln Ser His Ala Thr
1               5                   10                  15

Lys

<210> SEQ ID NO 8
<211> LENGTH: 17
<212> TYPE: PRT
<213> ORGANISM: Equus caballus
<220> FEATURE:
<223> OTHER INFORMATION: peptide of SEQ ID 6

<400> SEQUENCE: 8

Ala Gln Ser His Ala Thr Lys Gly His His Glu Ala Glu Leu Lys Pro
1               5                   10                  15

Leu

<210> SEQ ID NO 9
<211> LENGTH: 12
<212> TYPE: PRT
<213> ORGANISM: Equus caballus
<220> FEATURE:
<223> OTHER INFORMATION: peptide of SEQ ID 6

<400> SEQUENCE: 9

Gly His His Glu Ala Glu Leu Lys Pro Leu Ala Gln
1               5                   10
```